United States Patent [19]

Ciavattoni et al.

[11] 4,172,977
[45] Oct. 30, 1979

[54] FILM DRIVE MECHANISM FOR PANORAMIC DENTAL X-RAY MACHINE

[75] Inventors: Anthony Ciavattoni, Staten Island, N.Y.; John J. Flynn, Hazlet; Robert H. Cushman, Princeton, both of N.J.

[73] Assignee: Pennwalt Corporation, Philadelphia, Pa.

[21] Appl. No.: 889,708

[22] Filed: Mar. 24, 1978

[51] Int. Cl.² .............................................. G03B 41/16
[52] U.S. Cl. ............................ 250/439 P; 250/445 R
[58] Field of Search ........................ 250/439 P, 445 R

[56] References Cited

U.S. PATENT DOCUMENTS

| | | | |
|---|---|---|---|
| 3,867,636 | 2/1975 | Miyahara | 250/439 P |
| 3,908,126 | 9/1975 | Hudson et al. | 250/439 P |
| 4,039,837 | 8/1977 | Ohta et al. | 250/439 P |

Primary Examiner—Alfred E. Smith
Assistant Examiner—T. N. Grigsby

[57] ABSTRACT

Panoramic dental X-ray machine having an improved X-ray film drive mechanism for coordinating the speed of travel of the X-ray film with non-constant speeds of lateral chair shift to provide continuous radiographs of typical dental arch areas. The film drive mechanism employs a non-rotating cam slidably mounted about a motor shaft which rotates an assembly comprising a tubehead and a cassette holder assembly. The non-rotating cam is provided with adjacent opposing slope areas for programming decreased film travel speed when the incisors of the dental arch are being X-rayed. The film is traveling at its slowest rate of speed when the midline of the incisors is being X-rayed while the chair is traveling at its fastest rate of speed thereat. The chair shifts during the X-raying of the anterior region only. A cam follower is mounted to a plate which is pivotally mounted to the tubehead-cassette holder assembly for rotation with assembly. The plate also mounts cable and roller means which cooperate to urge the follower to constantly contact working surfaces and the adjacent opposing slope areas of the non-rotating cam. The chair shift speed is controlled by a rotating barrel cam having a continuous groove disposed therein, which rotating groove is contacted by a follower guide secured to a platform which mounts the chair.

15 Claims, 6 Drawing Figures

//4,172,977//

FILM DRIVE MECHANISM FOR PANORAMIC DENTAL X-RAY MACHINE

CROSS-RREFERENCE TO OTHER RELATED APPLICATIONS

Reference is hereby made to copending patent application, Ser. No. 856,423, filed Dec. 1, 1977, for "Panoramic Dental X-Ray Machine Base Excursion Drive Assembly," of A. Ciavattoni et al., assigned to the same assignee hereof.

STATEMENT OF THE INVENTION

The present invention relates to X-ray apparatus and more particularly concerns film drive mechanism which coordinates the speed of X-ray film travel with chair shift speeds to provide undistorted, continuous panoramic radiographs of dental arch areas.

BACKGROUND OF THE INVENTION

Panoramic radiographs may be obtained by directing an X-ray beam through an object to be X-rayed to a moving X-ray film while rotating the X-ray source and film about the object. In obtaining panoramic radiographs of the dental arch area however, compensation must be made for the fact that the curvature of the desired area of focus is generally not a true circle or ellipse.

Various cam mechanisms have been provided for varying the rate of film travel relative to the rate of travel of the X-ray source about the patient's head in order that the radiological projections occupy a distance on the film equal to the linear distance of a curved structure being X-rayed, such as a typical dental arch. These cam mechanisms, however, have usually required separate motors, i.e., one motor for rotating the tubehead-camera assembly about the patient's head, and the other motor for driving the cam mechanism which controls the rate of travel of the film. Such motors oftentimes lacked synchronization resulting in radiographs of doubtful value, or the entire tubehead-camera-film drive assembly required constant synchronous adjustment.

The present invention completely obviates the need for separate motors by providing a reliable film drive mechanism which operates in response to rotation of the tubehead-camera assembly which requires but a single motor for rotation.

BRIEF DESCRIPTION OF THE DRAWINGS

FIG. 4 is a plan view of the film drive mechanism of the invention.

DETAILED DESCRIPTION OF THE INVENTION

Figure 1:
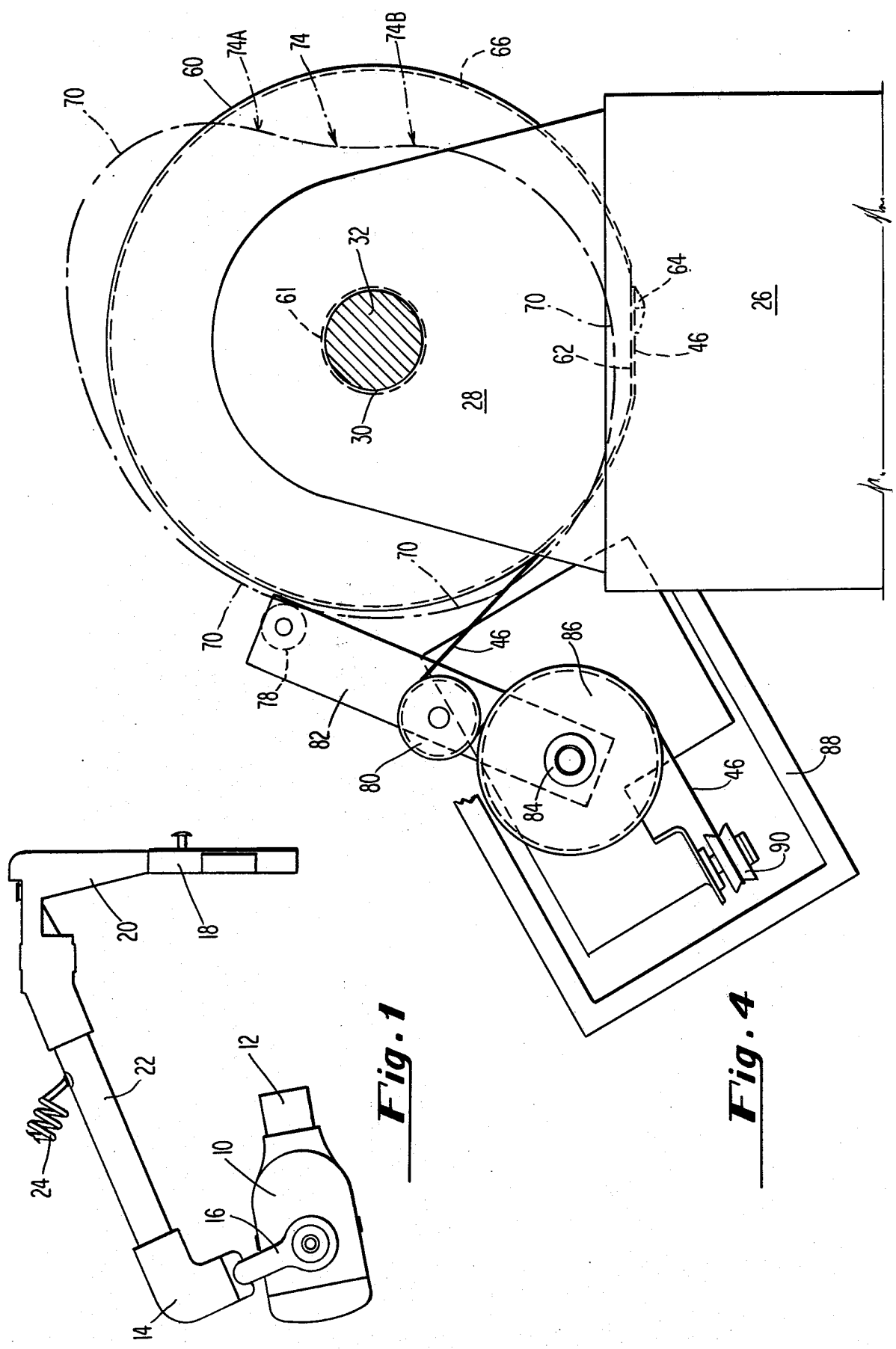
FIG. 1 is an assembly view of a tubehead-cassette holder assembly of a dental X-ray machine.

In FIG. 1, tubehead 10 includes cone 12 which focuses X-rays generated by an X-ray source within the tubehead. Trunnion 14 carries yoke 16 which permits limited tubehead rotation. A cassette holder assembly 18 contains X-ray film to be activated by the X-ray source. Cassette holder assembly 18 is supported by a cassette holder assembly support 20 which receives one end of horizontal arm 22, its other end received by trunnion 14. Horizontal arm 22 and cassette holder assembly support 20 maintain tubehead 10 and cassette holder assembly 18 a specified distance from each other and in alignment with the patient's head as they rotate about the patient. Power is supplied to the X-ray source through cable 24. The entire assembly abovedescribed is supported by assembly support arm 26, shown in FIG. 2. Assembly support arm 26 is received by a bifurcated casting 28 having a pair of vertically aligned holes 30—30 which receive output shaft 32 of a shaded pole motor (not shown). Shaft 32 rotates at a uniform speed of 1.83 rpm.

Cassette holder assembly 18 is conventional. It comprises cassette holder 40, cassette carriage 42 which travels within the cassette holder along rollers 44 when cable 46 and retrieving spring 48 cooperate, through cable roller 50 and other means, to move cassette carriage 42 and its film past vertical slit diaphragm 52 disposed centrally the front panel of the cassette holder assembly. Slit diaphragm 52, of course, permits the generated X-rays to pass therethrough for activation of the X-ray film.

Figure 2:
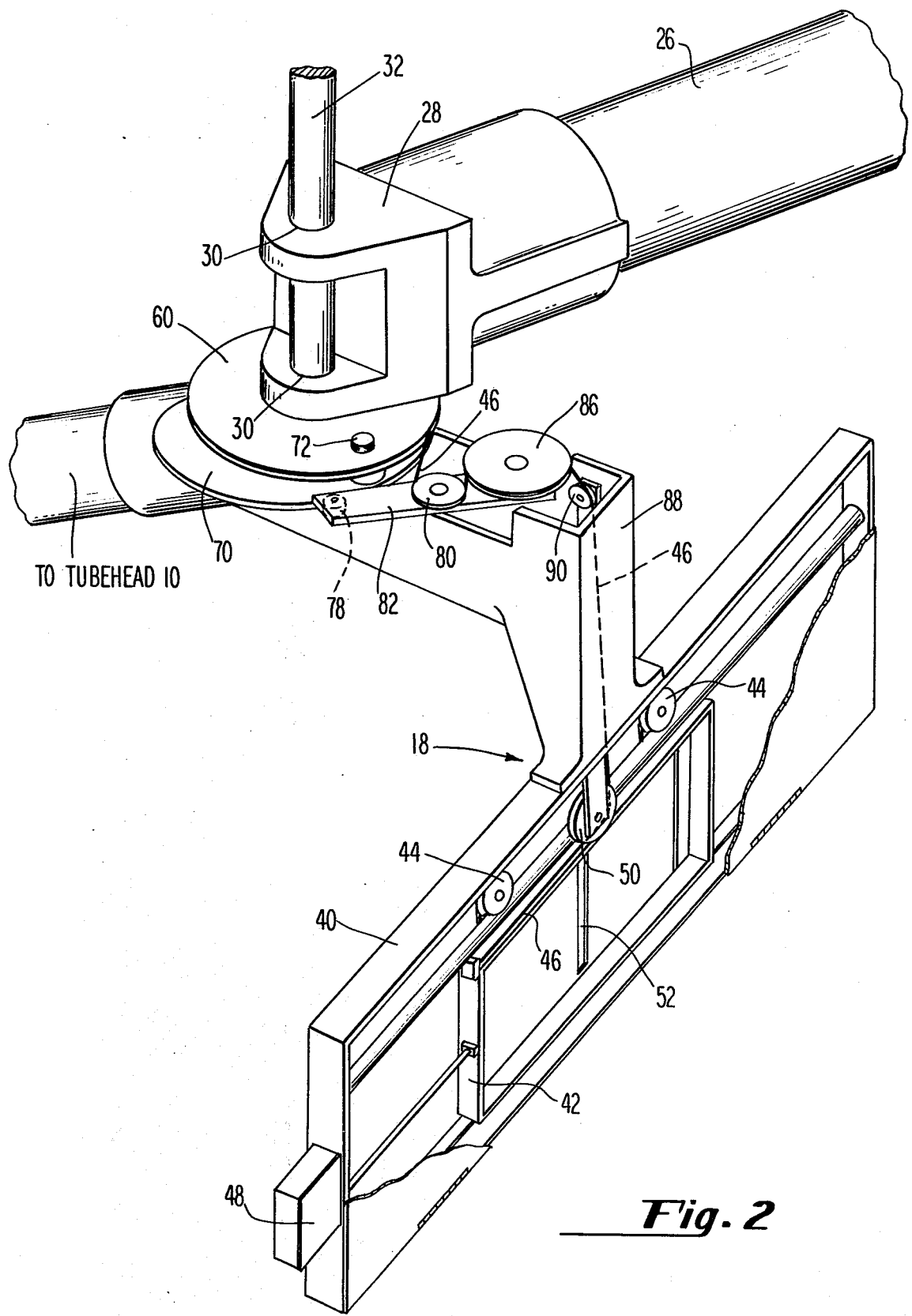
FIG. 2 is a perspective view of the film drive mechanism of the invention including the cassette holder assembly of FIG. 1.
Figure 3:
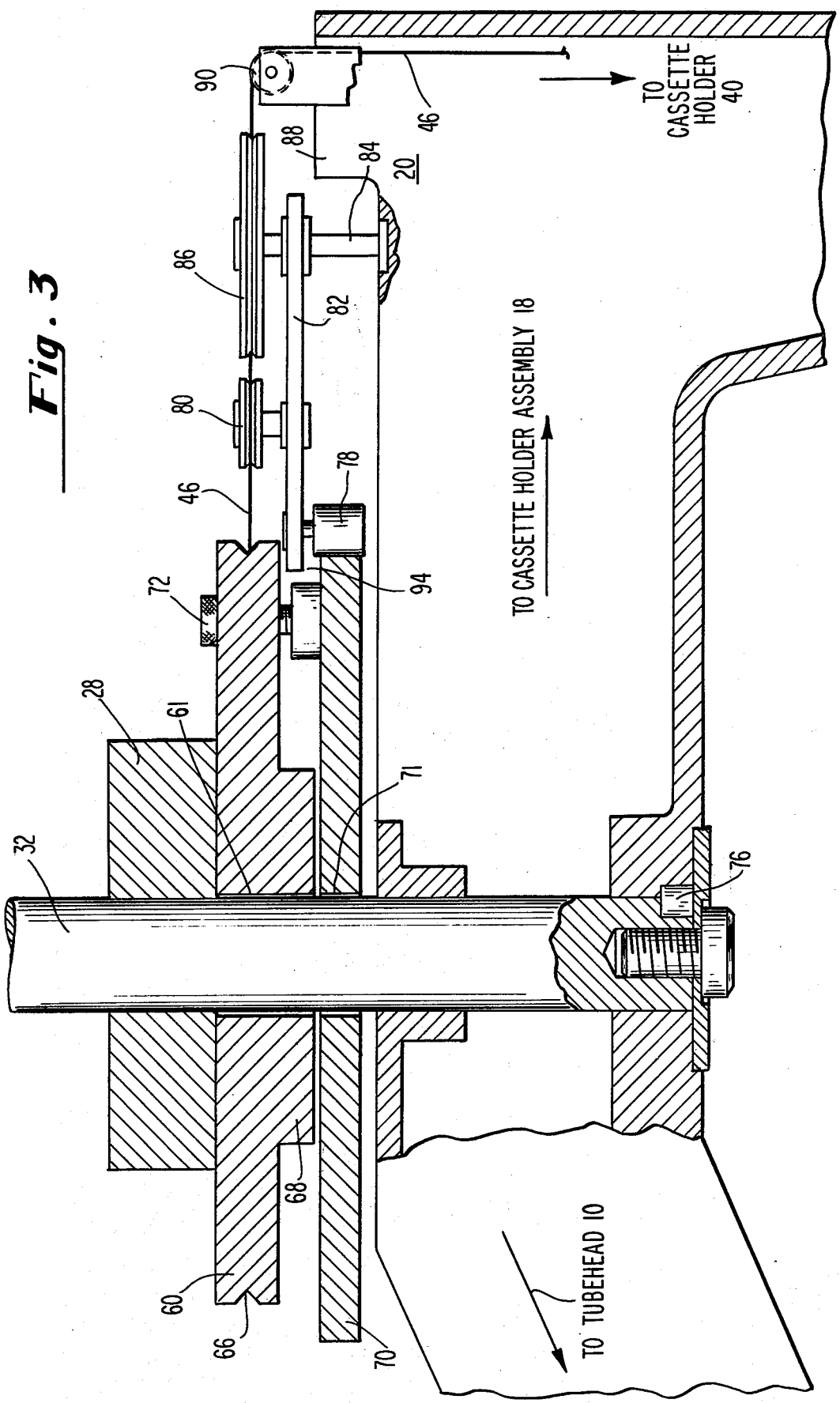
FIG. 3 is a partially sectioned elevational view of the film drive mechanism of the invention.

Referring to FIGS. 2, 3 and 4, storage disc 60 has a flattened edge 62 at a rear portion thereof. Storage disc 60 is fixedly mounted to casting 28 by suitable means (not shown). Cable 46 is secured to storage disc 60 at flattened edge 62 by cable connector 64. Storage disc 60 is provided with a circumferential groove 66 for maintaining cable 46 on the storage disc during rotation of tubehead 10 and cassette holder assembly 18 by shaft 32. Storage disc 60 is also provided with a spacer 68, either formed integrally therewith, or otherwise suitably affixed thereto. Function of spacer 68 is later described.

A cam 70 is disposed below storage disc 60 and is secured in operating position by means of a cam adjustment screw 72. By loosening screw 72, cam 70 may be rotated around shaft 32 for purposes of adjustment.

Cam 70 is provided with adjacent opposing slope surfaces shown generally at 74 for decreased speed of film travel during X-raying of the incisors or centrals area. Decrease of film travel speed at the centrals area is necessary since the centrals area is usually more arcuate in shape than the rear portions of the dental arch, i.e., the molar-bicuspid area. The slower film travel speed at the centrals area combined with proportionally faster chair shift speed at the centrals area, thus yields radiographs having substantially constant image magnification, and wherein each tooth's image is undistorted and occupies a distance on the film equal to, or proportional with, the linear distance of the teeth comprising the curved dental arch. The chair travels in a lateral direction opposing the general direction of travel of the tubehead.

Storage drum 60 and cam 70 do not rotate with shaft 32. Storage drum 60 and cam 70 have oversized bores 61 and 71 respectively which provide clearances for shaft 32 to rotate therewithin. Tubehead 10 and cassette holder assembly 18 rotate with shaft 32 through conventional key means 76. A cam follower 78 and V-guide roller 80 are rotatably mounted to opposite surfaces of a plate 82. Plate 82 is pivotally mounted about roller shaft 84 of another V-guide roller 86 which is pivotally mounted to an upper surface of cassette holder assembly support 20. Cassette holder assembly support 20 also mounts a pulley 90.

In assembling cable 46 to the present film drive mechanism, one end is secured to the storage disc at flattened edge 62. The cable is then threaded around the V of roller 80 in a counterclockwise direction (when viewed from above). Roller 86 is then similarly threaded, but in a clockwise direction, before threading into cassette holder 40 around pulley 90. Retrieving spring 48 receives the other end of cable 46.

Thus, by means of the mechanism described, follower 78 is constantly urged against cam 70, including its negative slope, when tubehead 10 and cassette holder assembly 18 rotate about the patient.

If the tubehead and cassette holder assembly rotate in a clockwise direction about the patient, the negative slope area 74A permits a substantially constant rate of deceleration of film travel speed until point 74 on cam 70 is reached. Point 74 coincides approximately with the center of the incisors area. Speed of travel of the film then increases at a substantially constant rate at positive slope 74B, or until the incisors have been X-rayed, at which point the original film travel speed is regained. Conversely, 74B designates a negative slope area, or an area of substantially constant rate of deceleration of film travel speed when the tubehead rotates about the patient in a counterclockwise direction, and 74A will thus represent a positive slope area.

Spacer 68 permits plate 82 to enter space 94 immediately below storage disc 60 when follower 78 is urged inwardly, or toward shaft 32. Absent space 94, plate 82 would contact storage disc 60 to prevent follower 78 from continuously following the working surfaces and adjacent opposing slopes of cam 70.

Figure 5:
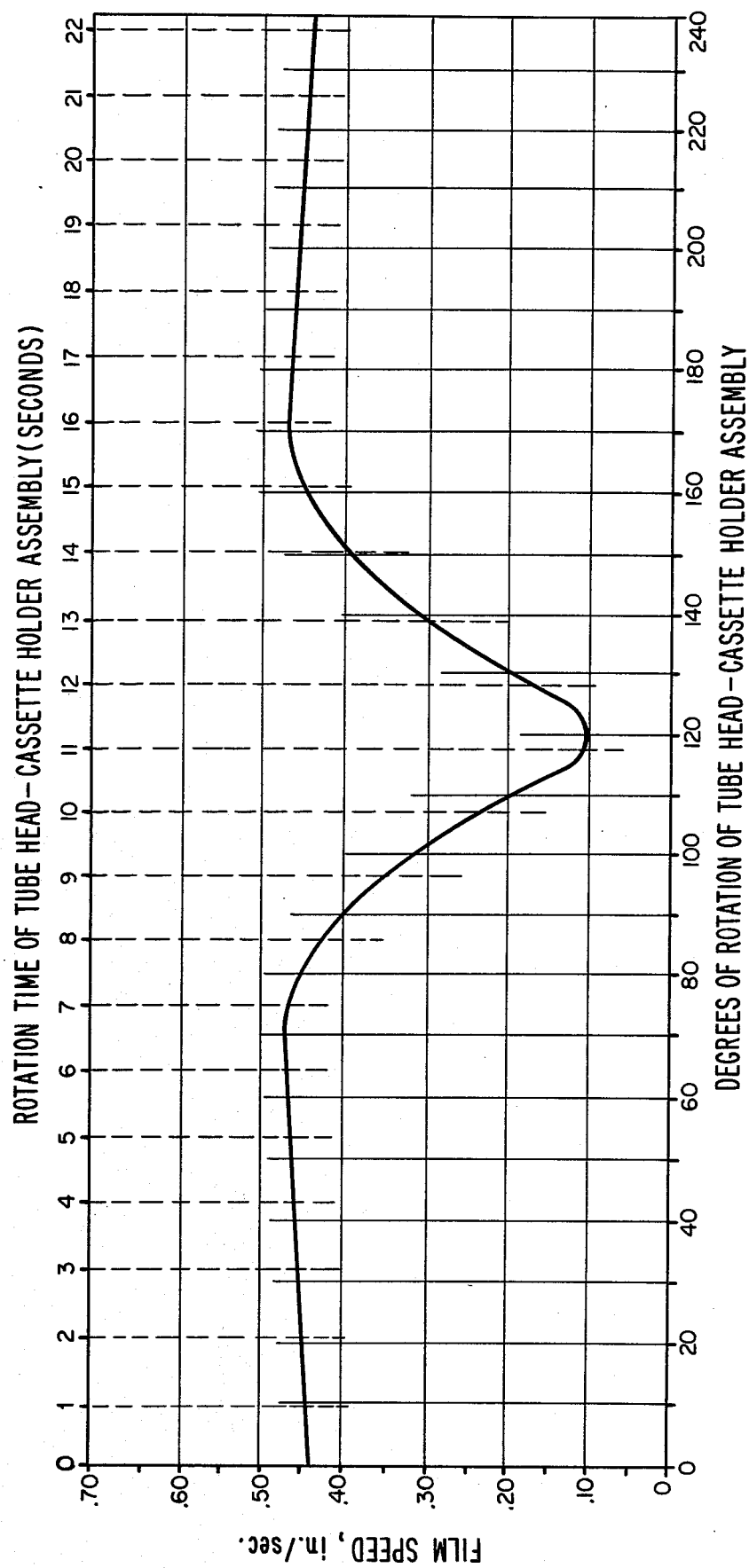
FIG. 5 is a graphic representation of film travel speed plotted against degrees of rotation of the tubehead-cassette holder assembly and time consumed for such rotation.

In the operation of the improved film drive mechanism, the patient is seated in the patient chair and the tubehead and cassette holder assembly positioned to start X-raying the left or right molar area. The film drive mechanism may be started simultaneously with the start of rotation of the tubehead and cassette holder assembly by a single switch. As shown in FIG. 5, the speed of travel of the film is approximately $\frac{1}{2}$ inch/second for about the first 70° of rotation of the tubehead and cassette holder assembly. After about 6$\frac{1}{2}$ seconds, or about 70° of tubehead travel, the film drive mechanism aforediscussed causes follower 78 to bear against negative slope area 74A, when the tubehead rotates in a clockwise direction about the patient, to decelerate film travel speed at a substantially constant rate to about 0.10 to 0.15 inches/second, represented approximately by point 74 on cam 70, which point coincides with the midline of the incisors. The speed of the film then starts to accelerate at a substantially constant rate for an additional 5$\frac{1}{2}$ seconds or so, or until the tubehead has rotated another 50°, at which time the film speed travel returns to its original speed of about $\frac{1}{2}$ inch/second.

The patient's chair is not shifted laterally at a constant speed. The chair starts its shift at about the start of the X-raying of the centrals, or about 70° after the tubehead starts its rotation, or when the film speed starts to decelerate. After about 120° of total tubehead travel, the speed of the chair starts to decelerate at a substantially constant rate for about 5 seconds, the deceleration of the chair being substantially inversely proportional to film speed acceleration thereat.

It should be appreciated that a decrease in film travel speed must be accompanied by a proportional increase in chair shift speed if true image portrayal of the incisors is to be achieved. That is, film travel speed is decreased when the centrals are being X-rayed, in accordance with the graph depicted in FIG. 5, to compensate for the arcuate shape of the centrals area. At the point where the film is travelling most slowly, or after approximately 11 seconds or 120° of rotation of the tubehead, the chair will be moving at its fastest speed. Were the chair to move at a constant speed while film speed travel has been decreased at the centrals, and not substantially inversely proportional to the film travel speed as contemplated by the present invention, the time of exposure to the X-rays at the centrals area would be excessive, thus resulting in distorted images. Additionally, the spinal column of patient is subjected to minimal irradiation since the chair shift speed is greatest when the X-ray source traverses the patient's spinal column.

Figure 6:
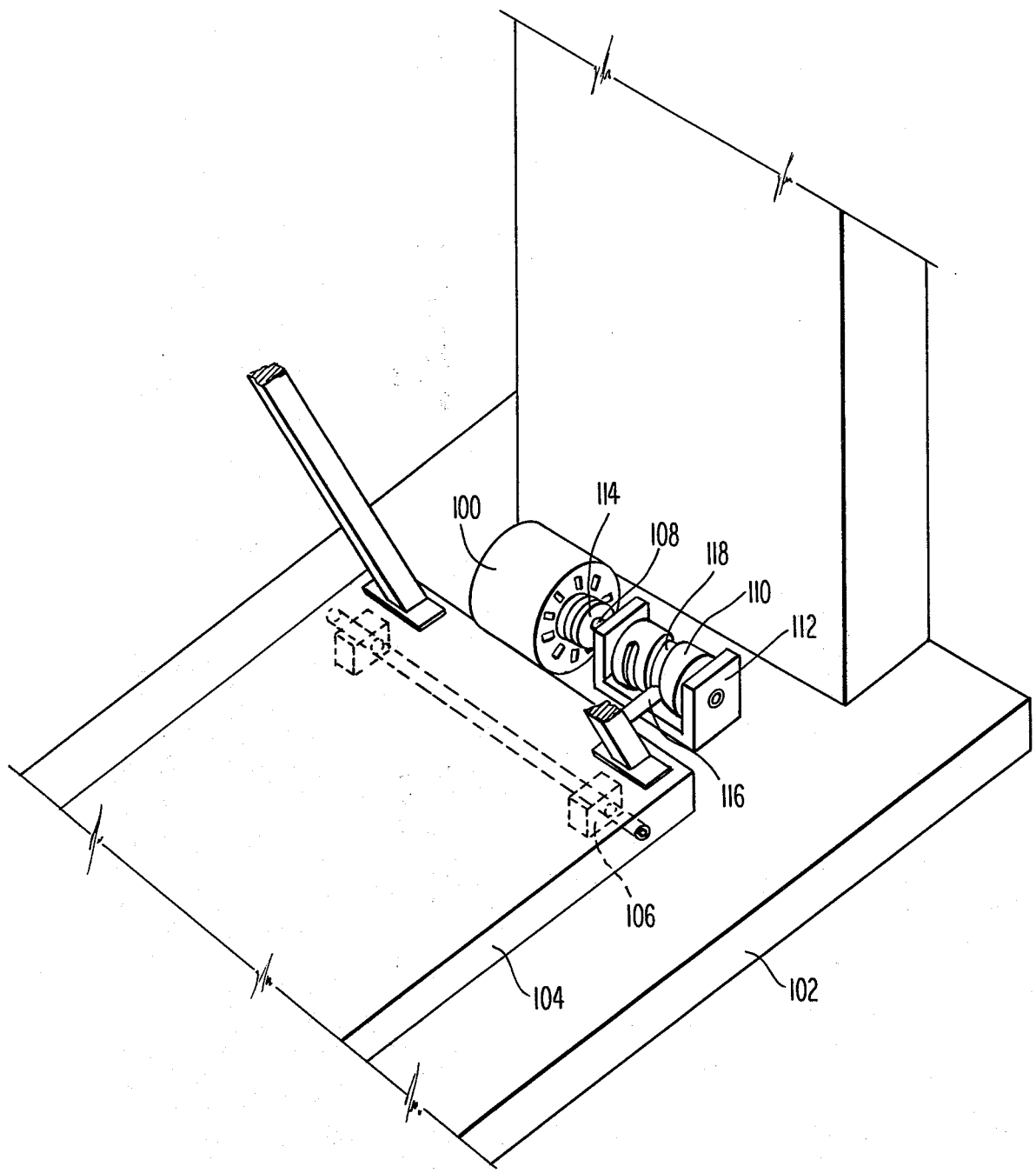
FIG. 6 is a perspective view of the chair shift mechanism of the invention.

Thus, in FIG. 6, an A.C. synchronous motor 100 is rigidly mounted to a base plate 102 which mounts chair platform 104 for lateral motion thereupon by means of a trolley arrangement 106. Motor 100 has an output shaft 108 which causes barrel cam 110 to rotate therewith. Barrel cam 110 is secured to base plate 102 by means of a suitable bracket assembly 112. Coupling member 114 couples shaft 108 and cam 110.

Chair platform 104 is provided with a follower guide 116 rigidly attached thereto which rides in groove 118 of cam 110 as cam rotates. Shaft 108 rotates at a speed of 3.66 rpm, or about double the speed of rotation of shaft 32 which rotates the tubehead and cassette holder assembly. A speed of rotation of shaft 108 considerably slower than about 3.66 rpm would impose an undue load on cam 110 and motor 100 by requiring a severe angle of contact, or an excessively large angle of contact, between the rotating groove and follower guide 116.

The severity of the angle with which follower guide 116 contacts rotating groove 118 determines the speed of chair shift, or the rate of travel of the chair. Thus, the chair would remain substantially motionless if the follower guide rode in a groove which was disposed perpindicular to the axis of rotation of shaft 108.

In the present invention, the substantially constant rate of deceleration of the chair is effected by follower guide 116 contacting groove 118 at a progressively smaller angle, or less severe angle, as groove 118 rotates. Conversely, the chair will acclerate its speed at a substantially constant rate when follower guide 116 contacts groove 118 at a progressively larger angle, or more severe angle, as groove 118 rotates. Motor 100 is reversible such that barrel cam 110 is capable of rotating in either direction.

Actuation of chair shift after about 70° of tubehead rotation, and stopping of the chair's movement after about 170° of tubehead rotation may readily be accomplished by cam-microswitch means. For example, a pair of rotating cams mounted on shaft 32 above bifurcated casting 28 could actuate respective microswitches which will close and open circuits to chair shift motor 100. Additional rotating cams mounted on shaft 32 could limit rotation of the tubehead 10 and cassette holder assembly 18 to about 240° of travel. Such cam-microswitch means are within the skill of the art, as well as circuitry therefore, and are not shown for purposes of simplification.

Although a flat cassette holder assembly is shown and described herein, the present invention may be used advantageously with a cylindrical type camera or cassette holder assembly, as shown in the cross-referenced copending application.

We claim:

1. In a panoramic dental X-ray machine for providing continuous radiographs of dental arch areas of a patient seated in a chair, said X-ray machine comprising
   (a) a tubehead containing an X-ray source and means to power said X-ray source,
   (b) a cassette holder assembly including a cassette carriage for holding film to be activated by said X-ray source, said cassette carriage including roller means to permit movement of said cassette carriage within said cassette holder assembly, said tubehead and said cassette holder assembly rotating as a unit and continuously in one direction for about 240°, said tubehead and said cassette holder assembly forming a tubehead-camera assembly which rotates in response to a uniform speed rotating output shaft operably connected thereto, said rotating output shaft supported for rotation by a stationary casting, in combination therewith of the improvement comprising
   film drive mechanism mounted on said tubehead-camera assembly responsive to rotation of said tubehead-camera assembly by said rotating output shaft, said film drive mechanism comprising
   storage means fixedly mounted to said stationary casting and about said rotating shaft,
   cam means spaced from said storage means and mounted about said rotating shaft in non-rotating relationship thereto and having adjacent opposing slope areas for decreased film travel speed when incisors of said dental arch area are being X-rayed,
   a plate pivotally mounted on said tubehead-camera assembly,
   means mounted on said plate responsive to said cam means,
   a cable communicating between said storage means and cassette carriage,
   means mounted within said cassette holder assembly urging said cable towards said cassette carriage, and
   other means mounted on said plate in cooperating relationship with said cable for urging said means responsive to said cam means to constantly bear against working surfaces and said adjacent opposing slope areas of said cam means when said tubehead-camera assembly rotates about said patient and said cam means whereby said cassette carriage and film are caused to travel along said roller means within said cassette holder assembly at various speeds in accordance with said working surfaces and said adjacent opposing slope areas of said cam means.

2. X-ray machine as in claim 1 wherein said adjacent opposing slope areas comprise a negative slope and a positive slope, said negative slope permitting a substantially constant rate of deceleration of film travel speed when said means responsive to said cam means bears thereagainst, and said positive slope permitting a substantially constant rate of acceleration of film travel speed when said means responsive to said cam means bears thereagainst.

3. X-ray machine as in claim 2 further characterized by chair shift means for laterally shifting said chair at a substantially constant rate of acceleration coinciding proportionally with said substantially constant decelerating rate of film travel speed, and a substantially constant rate of deceleration of said chair shift speed coinciding proportionally with said substantially constant acceleration rate of film travel speed, said chair shift speed being greatest when X-raying the midline of the incisors of said dental arch area, said chair shifting in a direction opposing general direction of travel of said tubehead.

4. X-ray machine as in claim 3 wherein said storage means comprises a circular disc having a circumferential groove disposed centrally about its periphery for receiving said cable therearound.

5. X-ray machine as in claim 4 wherein said means mounted within said cassette holder assembly for urging said cable towards said cassette holder is a retrieving spring.

6. X-ray machine as in claim 5 further characterized by said storage disc having a flattened edge disposed at a rear portion thereof, said cable having one of its ends secured to said storage disc at said flattened edge and the other end of said cable secured to said retrieving spring.

7. X-ray machine as in claim 6 wherein said other means comprises a pair of rollers having circumferential V-grooves disposed about their peripheries, said cable being threaded around said rollers in said V-grooves in cooperating relationship to urge said means mounted on said plate responsive to said cam means to constantly bear against working surfaces and said adjacent opposing slope areas of said cam means.

8. X-ray machine as in claim 7 wherein said means mounted on said plate responsive to said cam means is a cam follower.

9. X-ray machine as in claim 8 wherein said cable secured to said storage disc flattened edge is first threaded around one of said rollers closer to said cam follower in a counterclockwise direction, and thence around said other roller in an opposite direction, said directions of rotation being designated when looking down upon said rollers.

10. X-ray machine as in claim 9 wherein said storage disc is provided with spacer means centrally therebelow, said spacer means providing a space between said storage disc and said cam means for entry of said plate upon rotation of said tubehead-camera assembly about said patient and said cam means.

11. X-ray machine as in claim 10 further characterized by adjustment means mounted on said storage disc for contacting said cam means to maintain said cam means in a selected position.

12. X-ray machine as in claim 9 wherein a pulley is mounted between said cassette holder assembly and said roller threaded by said cable in a clockwise direction, said pulley guiding said cable into said cassette holder from said clockwise threaded roller.

13. X-ray machine as in claim 3 wherein said chair shift means comprises
   a base plate,
   a chair platform slidably mounted above said base plate, said platform including a follower guide extending therefrom and rigidly attached thereto, a barrel cam supported on said base plate, said barrel cam having a spiral groove provided therein for receiving said follower guide, means to rotate said barrel cam, said follower guide riding within said spiral groove of said barrel cam to laterally shift said chair at said substantially constant rates of deceleration and acceleration.

14. X-ray machine as in claim 13 wherein said substantially constant rate of deceleration of said chair is provided by said groove contacting said follower guide at a progressively smaller angle as said groove rotates and said substantially constant rate of acceleration of said chair is provided by said groove contacting said follower guide at a progressively greater angle as said groove rotates.

15. X-ray machine as in claim 13 wherein said means to rotate said barrel cam has an output shaft coupled to said barrel cam for rotating said barrel cam at about 3.66 rpm.